United States Patent [19]

Yamanaka et al.

[11] Patent Number: 5,021,432

[45] Date of Patent: Jun. 4, 1991

[54] BENZOPYRAN COMPOUND AND ITS PHARMACEUTICAL USE

[75] Inventors: Tsutomu Yamanaka; Toshio Seki; Tohru Nakajima; Osamu Yaoka, all of Nakatsu, Japan

[73] Assignee: Yoshitomi Pharmaceutical Industries, Ltd., Osaka, Japan

[21] Appl. No.: 340,271

[22] Filed: Apr. 19, 1989

[30] Foreign Application Priority Data

Apr. 26, 1988 [JP] Japan .................... 63-103222
Nov. 1, 1988 [JP] Japan .................... 63-278142
Nov. 25, 1988 [JP] Japan .................... 63-299190

[51] Int. Cl.⁵ .............. A61K 31/44; A61K 31/38; C07D 405/12; C07D 333/32
[52] U.S. Cl. .................. 514/337; 549/404; 549/399; 549/60; 546/269; 546/256; 514/456
[58] Field of Search .......... 549/404, 399, 60; 546/269, 256; 514/333, 337, 456, 444

[56] References Cited

FOREIGN PATENT DOCUMENTS 0095316 11/1983 European Pat. Off. .
0126311 11/1984 European Pat. Off. .
0172352  2/1986 European Pat. Off. .
0250077 12/1987 European Pat. Off. .

OTHER PUBLICATIONS

Ashwood et al., "J. Med. Chem", 29 (11), 2194-2201 (1986).

*Primary Examiner*—Nicky Chan
*Attorney, Agent, or Firm*—Wenderoth, Lind & Ponack

[57] ABSTRACT

A benzopyran compound of the general formula (I)

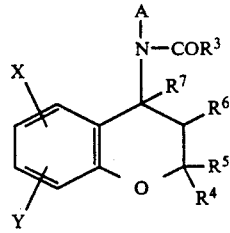

wherein A represents $-OR^1$ or $-NH-COR^2$ (wherein $R^1$ represents hydrogen, a lower alkyl, formyl, an alkanoyl, an aroyl or an aralkyl and $R^2$ represents hydrogen, a lower alkyl, a lower alkoxy, amino, mono- or di-lower alkylamino, an amino-lower alkyl, a hydroxy-lower alkyl, a halo-lower alkyl, a lower alkoxy-lower alkyl, an acyloxy-lower alkyl, a lower alkoxy-carbonyl-lower alkyl, an aryl or a heteroaryl); $R^3$ represents hydrogen, a lower alkyl, a lower alkoxy, amino, a mono- or di-lower alkylamino, an amino-lower alkyl, a hydroxy-lower alkyl, a halo-lower alkyl, a lower alkoxy-lower alkyl, an acyloxy-lower alkyl, a lower alkoxycarbonyl-lower alkyl, an aryl or a heteroaryl, or $R^2$ and $R^3$ combinedly together form an alkylene having 1 to 2 carbon atoms; $R^4$ and $R^5$ are the same or different, and respectively represent hydrogen or a lower alkyl, or combinedly together form an alkylene having 2 to 5 carbon atoms; $R^6$ represents hydroxyl group, formyloxy, an alkanoyloxy, a haloalkanoyloxy, a lower alkoxycarbonyloxy, an aroyloxy, a heteroaroyloxy, carbamoyloxy, a mono- or di-lower alkylcarbamoyloxy and $R^7$ represents hydrogen, or $R^6$ and $R^7$ combinedly together form a bond and X and Y are the same or different, and respectively represent hydrogen, halogen, nitro, cyano, a lower alkyl, a lower alkoxy, a halo-lower alkyl, carboxyl, formyl, and alkanoyl, an aroyl, a halo-alkanoyl, carbamoyl, a lower alkylsulfinyl, an arylsulfinyl, a lower alkylsulfonyl, and arylsulfonyl, sulfonamido or a mono- or di-lower alkylsulfonamido, or their pharmaceutically acceptable salts and its pharmaceutical use.

The compounds of the present invention exhibit remarkable and long lasting antihypertensive actions and peripheral vascular relaxant actions and therefore are useful as therapeutic medicines for hypertensive. Since they also display selective coronary vasodilating actions and the duration of actions are very long, they are of use as therapeutic medicines for cardiovascular disturbances such as angina pectoris and cardiac insufficiency.

7 Claims, No Drawings

BENZOPYRAN COMPOUND AND ITS PHARMACEUTICAL USE

BACKGROUND ART

This invention relates to novel benzopyran compounds and their pharmaceutically acceptable salts which possess remarkable and durable antihypertensive actions, coronary vasodilating actions and relaxant actions on vascular smooth muscles and the other smooth muscles and pharmaceutical uses thereof.

In U.S. Pat. No. 4,446,113, there is disclosed 6-cyano-3,4-dihydro-2,2-dimethyl-trans-4-(2-oxo-1-pyrrolidinyl)-2H-1-benzopyran-3-ol(BRL-34915). In European Patent Publication (Laid-open) Gazzette No. 273262/1988, British Patent Publication Gazzette No. 2204868/1988 and European Patent Publication (Laid-open) Gazzette No. 296975/1988, there are disclosed a group of 4-substituted benzopyran compounds having antihypertensive actions, smooth muscle-relaxant actions and the like.

SUMMARY OF THE INVENTION

It was found that novel benzopyran compound having a N-acyl-N-oxy-substituted amino group or hydrazine group at the 4-position possessed remarkable and durable hypotensive actions and coronary vasodilating actions, and also vascular smooth muscles- and the other smooth muscle-relaxant actions, which resulted in the accomplishment of the present invention.

DETAILED DESCRIPTION OF THE INVENTION

This invention relates to the benzopyran compounds of the general formula (I)

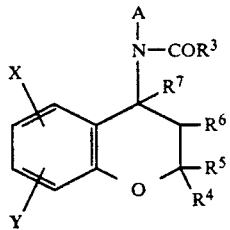

wherein A represents $-OR^1$ or $-NH-COR^2$ (wherein $R^1$ represents hydrogen, a lower alkyl, formyl, an alkanoyl, an aroyl or an aralkyl and $R^2$ represents hydrogen, a lower alkyl, a lower alkoxy, amino, mono- or di-lower alkylamino, an amino-lower alkyl, a hydroxy-lower alkyl, a halo-lower alkyl, a lower alkoxy-lower alkyl, an acyloxy-lower alkyl, a lower alkoxycarbonyl-lower alkyl, an aryl or a heteroaryl); $R^3$ represents hydrogen, a lower alkyl, a lower alkoxy, amino, a mono- or di-lower alkylamino, an amino-lower alkyl, a hydroxy-lower alkyl, a halo-lower alkyl, a lower alkoxy-lower alkyl, an acyloxy-lower alkyl, a lower alkoxycarbonyl-lower alkyl, an aryl or a heteroaryl, or $R^2$ and $R^3$ combinedly together form an alkylene having 1 to 2 carbon atoms; $R^4$ and $R^5$ are the same or different, and respectively represent hydrogen or a lower alkyl, or combinedly together form an alkylene having 2 to 5 carbon atoms; $R^6$ represents hydroxyl group, formyloxy, an alkanoyloxy, a haloalkanoyloxy, a lower alkoxycarbonyloxy, an aroyloxy, a heteroaroyloxy, carbamoyloxy, a mono- or di-lower alkylcarbamoyloxy and $R^7$ represents hydrogen, or $R^6$ and $R^7$ combinedly together form a bond and X and Y are the same or different, and respectively represent hydrogen, halogen, nitro, cyano, a lower alkyl, a lower alkoxy, a halo-lower alkyl, carboxyl, formyl, an alkanoyl, an aroyl, a haloalkanoyl, carbamoyl, a lower alkylsulfinyl, an arylsulfinyl, a lower alkylsulfonyl, an arylsulfonyl, sulfonamido or a mono- or di-lower alkylsulfonamido, or their pharmaceutically acceptable salts and their pharmaceutical use.

In the above-mentioned definitions, halogens mean chlorine, bromine, fluorine and iodine; lower alkyls mean straight- or branched-chain alkyls having 1 to 6 carbon atoms, which are exemplified by methyl, ethyl, propyl, isopropyl, butyl, isobutyl, tert-butyl, pentyl, isopentyl, hexyl and the like; amino-lower alkyls mean straight- or branched-chain aminoalkyls having 1 to 6 carbon atoms, which are examplified by aminomethyl, 2-aminoethyl, 3-aminopropyl, 1-aminomethylethyl, 4-aminobutyl, 5-aminopentyl, 6-aminohexyl and the like; hydroxy-lower alkyls mean straight- or branched-chain hydroxyalkyl having 1 to 6 carbon atoms, which are exemplified by hydroxymethyl, 2-hydroxyethyl, 3-hydroxypropyl, 1-hydroxymethylethyl, 4-hydroxybutyl, 5-hydroxypentyl, 6-hydroxyhexyl and the like; halo-lower alkyls mean straight- or branched-chain halogenated alkyls having 1 to 4 carbon atoms, which are exemplified by chloromethyl, bromomethyl, fluoromethyl, iodomethyl, dichloromethyl, dibromomethyl, difluoromethyl, diiodomethyl, trifluoromethyl, chloroethyl, bromoethyl, fluoroethyl, iodoethyl, difluoroethyl, trifluoroethyl, chloropropyl, bromopropyl, fluoropropyl, iodopropyl, difluoropropyl, trifluoropropyl, chlorobutyl, bromobutyl, fluorobutyl, iodobutyl, difluorobutyl, trifluorobutyl and the like; lower alkoxys mean straight- or branched-chain alkoxys having 1 to 6 carbon atoms, which are exemplified by methoxy, ethoxy, propoxy, isopropoxy, butoxy, isobutoxy, tert-butoxy, pentyloxy, hexyloxy and the like; lower alkoxy-lower alkyls mean alkoxyalkyls having, as the alkoxy moieties and the alkyl moieties, respectively straight- or branched-chain ones having 1 to 4 carbon atoms, which are exemplified by methoxymethyl, 2-methoxyethyl, 3-methoxypropyl, 4-methoxybutyl, ethoxymethyl, propoxymethyl, butoxymethyl and the like; lower alkoxycarbonyl-lower alkyls mean alkoxycarbonylalkyls having, as the alkoxy moieties and the alkyl moieties, respectively straight- or branched-chain ones having 1 to 4 carbon atoms, which are exemplified by methoxycarbonylmethyl, 2-methoxycarbonylethyl, 3-methoxycarbonylpropyl, 4-methoxycarbonylbutyl, ethoxycarbonylmethyl, propoxycarbonylmethyl, butoxycarbonylmethyl, and the like; aralkyls means aralkyls having, as the alkyl moieties, straight- or branched-chain alkyls having 1 to 4 carbon atoms, which are exemplified by benzyl, 2-phenylethyl, 3-phenylpropyl, 4-phenylbutyl naphthylmethyl 2-naphthylethyl, 3-naphthylpropyl, 4-naphthylbutyl, and benzyls, 2-phenylethyls, 3-phenylpropyls, 4-phenylbutyls, naphthylmethyls, 2-naphthylethyls, 3-naphthylpropyls and 4-naphthylbutyls each of which has on the aromatic ring at least one substituent selected from among halogens, lower alkyls, lower alkoxys, hydroxyl group, trifluoromethyl, cyano, nitro, amino, and the like; aryls mean phenyl naphthyl, and phenyls and naphthyls each of which has on the aromatic ring at least one substituent selected from among halogens (chlorine, bromine, iodine, fluorine), lower alkyls, lower alkoxys (straight- or branched-chain alkoxys having 1 to 4 carbon atoms, exemplified by methoxy, ethoxy, propoxy, isopropoxy, butoxy, isobutoxy and tert-butoxy), hydroxyl group, trifluoromethyl, cyano, nitro and amino; heteroaryls include, for example, furyl (2-furyl, 3-furyl), pyridyl (2-pyridyl, 3-pyridyl, 4-pyridyl) and thienyl (2-thienyl, 3-thienyl), and furyls, pyridyls and thienyls each of which has on the heterering at least one substituent selected from among halogens, lower alkyls, lower alkoxys, hydroxyl group, trifluoromethyl, cyano, nitro and amino; alkanoyls mean straight- or branched-chain alkyanoyls having 2 to 5 carbon atoms, optionally substituted by phenyl, which are exemplified by acetyl, propionyl, butyryl, valeryl, pivaloyl, phenylacetyl, phenylpropionyl, phenylbutyryl; aroyls mean benzoyl, naphthoyl and the like; mono- or di-lower alkylaminos mean mono- or dialkylaminos having, as the alkyl moieties, straight- or branched-chain alkyls having 1 to 6 carbon atoms, which are exemplified by methylamino, ethylamino, propylamino, isopropylamino, butylamino, isobutylamino, tert-butylamino, pentylamino, hexylamino, dimethylamino, diethylamino, dipropylamino, diisopropylamino, dibutylamino, diisobutylamino, di-tert-butylamino, dipentylamino, dihexylamino and the like; alkylenes having one to two carbon atoms include methylene, ethylene and the like and alkylenes having 2 to 5 carbon atoms include ethylene, trimethylene, propylene, tetramethylene, pentamethylene and the like; alkanoyloxies mean alkanoyloxies having, as the alkanoyl moieties, straight- or branched-chain alkanoyls having 2 to 5 carbon atoms optionally substitued by phenyl, which are exemplified by acetyloxy, propionyloxy, butyryloxy, valeryloxy, pivaloyloxy, phenylacetyloxy, phenylpropionyloxy, phenylbutyryloxy and the like; haloalkanoyloxies mean those having halogenated alkanoyls having, as the alkanoyl moieties, straight- or branched-chain alkanoyls having 2 to 5 carbon atoms, which are exemplified by chloroacetyloxy, bromoacetyloxy, fluoroacetyloxy, iodoacetyloxy, dichloroacetyloxy, dibromoacetyloxy, difluoroacetyloxy, diiodoacetyloxy, trifluoroacetyloxy, chloropropionyloxy, bromopropionyloxy, fluoropropionyloxy, iodopropionyloxy, difluoropropionyloxy, trifluoropropionyloxy, chlorobutyryloxy, bromobutyryloxy, fluorobutyryloxy, iodobutyryloxy, difluorobutyryloxy, trifluorobutyryloxy, fluorovaleryloxy, fluoropivaloyloxy and the like; lower alkoxy carbonyloxys mean alkoxycarbonyloxys having, as the alkoxy moieties, straight- or branched-chain alkoxys having 1 to 6 carbon atoms, which are exemplified by methoxycarbonyloxy, ethoxycarbonyloxy, propoxycarbonyloxy, isopropoxycarbonyloxy, butoxycarbonyloxy, isobutoxycarbonyloxy, tert-butoxycarbonyloxy, pentyloxycarbonyloxy, hexyloxycarbonyloxy and the like; aroyloxys include benzoyloxy, naphthoyloxy and the like; heteroaroyloxys include 2-furoyloxy, 3-furoyloxy, nicotinoyloxy, isonicotinoyloxy, 4-pyridylcarbonyloxy, 2-thenoyloxy, 3-thenoyloxy and the like; mono-or di-lower alkylcarbamoyloxys mean mono- or dialkylcarbamoyloxys having, as the alkyl moieties, straight- or branched-chain alkyls having 1 to 6 carbon atoms, which are exemplified by methylcarbamoyloxy, ethylcarbamoyloxy, propylcarbamoyloxy, isopropylcarbamoyloxy, butylcarbamoyloxy, isobutylcarbamoyloxy, tert-butylcarbamoyloxy, pentylcarbamoyloxy, hexylcarbamoyloxy, dimethylcarbamoyloxy, diethylcarbamoyloxy, dipropylcarbamoyloxy, diisopropylcarbamoyloxy, dibutylcarbamoyloxy, diisobutylcarbamoyloxy, di-tert-butylcarbamoyloxy, dipentylcarbamoyloxy, dihexylcarbamoyloxy and the like; lower alkylsulfinyls include alkylsulfinyls having, as the alkyl moieties, straight- or branched-chain alkyls having 1 to 6 carbon atoms, which are exemplified by methylsulfinyl, ethylsulfinyl, propylsulfinyl, isopropylsulfinyl, butylsulfinyl, isobutylsulfinyl, tert-butylsulfinyl, pentylsulfinyl, hexylsulfinyl and the like; arylsulfinyls include, for example, phenylsulfinyl, naphthylsulfinyl and phenylsulfinyls and naphthylsulfinyls each of which has on the aromatic ring at least one substituent selected from among halogens (chlorine, bromine, iodine, fluorine), lower alkyls, lower alkoxys, hydroxy group, trifluoromethyl, cyano, nitro, and amino; lower alkylsulfonyls include alkylsulfonyls having, as the alkyl moieties, straight- or branched-chain alkyls having 1 to 6 carbon atoms, which are exemplified by methylsulfonyl, ethylsulfonyl, propionylsulfonyl, isopropylsulfonyl, butylsulfonyl, isobutylsulfonyl, tert-butylsulfonyl, pentylsulfonyl, hexylsulfonyl and the like; arylsulfonyls include, for example, phenylsulfonyl, naphthylsulfonyl and phenylsulfonyls and naphthylsulfonyls each of which has on the aromatic ring at least one substituent selected from among halogens (chlorine, bromine, iodine, fluorine), lower alkyls, lower alkoxys, hydroxyl group, trifluoromethyl, cyano, nitro and amino and mono- or di-lower alkylsulfonamidos mean mono- or di-alkylsulfonamidos having, as the alkyl moieties, straight- or branched-chain alkyls having 1 to 6 carbon atoms, which are exemplified by methylsulfonamido, ethylsulfonamido, propylsulfonamido, isopropylsulfonamido, butylsulfonamido, isobutylsulfonamido, tert-butylsulfonamido, pentylsulfonamido, hexylsulfonamido, dimethylsulfonamido, diethylsulfonamido, dipropylsulfonamido, diisopropylsulfonamido, dibutylsulfonamido, diisobutylsulfonamido, di-tert-butylsulfonamido, dipentylsulfonamido, dihexylsulfonamido and the like.

The compounds of the present invention can be prepared by, for example, the per se known methods.

The compound of the formula (I) wherein A is —OR$^1$ can be prepared by the following method.

METHOD 1

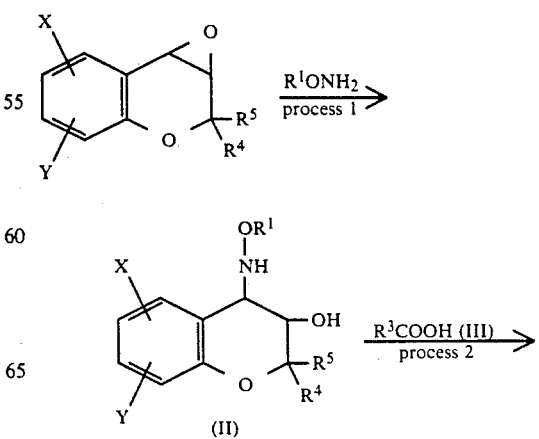

-continued

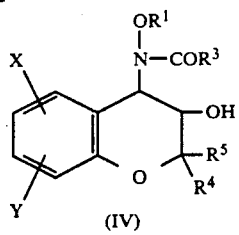

[in the above reaction formulae, $R^1$ represents a protective group for hydroxyl group (lower alkyls, lower alkoxy-lower alkyls, benzyl, substituted benzyls, diphenylmethyl, trityl, and the like) and the other symbols are as defined above.]

The reaction of process 1 is usually conducted at 10°-100° C. in a solvent such as an alcohol having 1 to 4 carbon atoms, particularly methanol, ethanol, propanol and the like. The reaction proceeds particularly smoothly when conducted under reflux in said solvent.

In the reaction of process 2, in the case where the compound of the general formula (III) is a free carboxylic acid, the reaction is conducted under cooling, at room temperature or under heating in an inert solvent in the presence of a condensing agent such as dicyclohexylcarbodiimide, titanium tetrachloride, a phosphorus halogenide (phosphorus trichloride, phosphorus oxychloride etc.), diethylchlorophosphite, o-phenylenechlorophosphite, ethyldichlorophosphite and the like. The reaction can be carried out by allowing a phosphorus halogenide in advance to act on the compound (II) in an inert solvent, followed by the condensation reaction with the compound (III). For example, in the case where the phosphorus halogenide is phosphorus trichloride, about ⅓ mol phosphorus trichloride is allowed to act on the compound (II) in an inert solvent in the presence of a tertiary base such as triethylamine, pyridine, N,N-dimethylaniline or the like under cooling or at room temperature, followed by the reaction with the compound (III) in an inert solvent at room temperature or under heating, preferably while heating under reflux.

In the case where an acid halide such as an acid chloride, or an acid bromide, as a reactive derivative of the carboxylic acid of the compound (III), is used, the reaction can be conducted in an inert solvent in the presence of a tertiary base such as triethylamine, pyridine or N,N-dimethylaniline under cooling or at room temperature, or in water in the presence of an alkali such as sodium hydroxide or potassium hydroxide under cooling or at room temperature.

In the case where a mixed acid anhydride such as an alkyl carbonate mixed acid anhydride, an alkyl phosphate mixed acid anhydride, an alkyl phosphite mixed acid anhydride or a mixed acid anhydride with sulfuric acid, as a reactive derivative of the compound (III), is used, the reaction can be conducted in an inert solvent in the presence of tertiary base such as triethylamine, pyridine or N,N-dimethylaniline under cooling, at room temperature or under heating.

In the case where an active amide such as acid imidazolide, acid pyrrolidide or 2,4-dimethylpyrazolide, as a reactive derivative of the compound (III), is used, the reaction can be conducted in an inert solvent at room temperature or under heating.

In the case where an active ester such as methyl ester, ethyl ester, p-nitrophenyl ester or p-chlorophenyl ester, as a reactive derivative of the compound (III), is used, the reaction can be conducted in an inert solvent at room temperature or while heating, preferably while heating under reflux.

As the inert solvents, mention may be made of benzene, toluene, xylene, methanol, ethanol, isopropylalcohol, ethyl ether, dioxane, tetrahydrofuran, chloroform, dichloromethane, dichloroethane, hexamethylphosphoric triamide, diethylene glycol, dimethylformamide and the like or their mixed solvents. When the compound (III) is a reactive derivative, the solvent is appropriately selected depending upon the species of the reactive derivative.

The deprotection of the protected hydroxyl group can be conducted by conducting hydrogenolysis under ordinary pressure with the use of palladium-carbon in a suitable solvent (ethanol, methanol, dimethylformamide, dioxane etc.), or by allowing hydrobromic acid-acetic acid, aluminium chloride, methionine-methanesulfonic acid, a lower alkyl disulfidealuminium chloride or the like to act thereon. The reaction can be conducted in a suitable solvent (acetic acid, methylene chloride, chloroform, dichloroethane, methansulfonic acid etc.) at room temperature to under reflux of the solvent. The reaction usually proceeds for 1 to 24 hours. Further, the thus obtained compound of the formula (IV) is subjected, if necessary, to deprotection under appropriate conditions to give the corresponding compound (I) wherein $R^1$ is hydrogen.

The compound of the general formula (I) wherein $R^1$ is a group as defined above other than hydrogen can be produced by reacting the compound of the formula (I) wherein $R^1$ is hydrogen with the compound of the general formula.

$$R^{1'}-Y \qquad (V)$$

(wherein $R^{1'}$ is a group as defined above for $R^1$ other than hydrogen and Y is a reactive functional group such as a halogen, an acyloxy, an alkylsulfonyloxy or an arylsulfonyloxy).

The reaction usually proceeds in an inert solvent (water, methanol, ethanol, dimethylformamide, or their mixed solvent, preferably aqueous ethanol) in the presence of a base (sodium hydroxide, potassium hydroxide, sodium hydride, potassium hydride, sodium methoxide, sodium ethoxide, sodium carbonate, potassium carbonate, metal sodium, triethylamine, pyridine etc.) at a temperature ranging from about 0° C. to the boiling point of the used solvent, preferably at 20°-80° C., for about 10 minutes to 24 hours, preferably 30 minutes to 3 hours.

The compound of the general formula (I), wherein A is —NH—COR$^2$ can be prepared by the following method.

METHOD 2

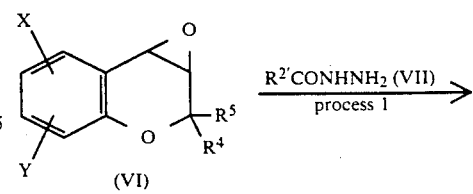

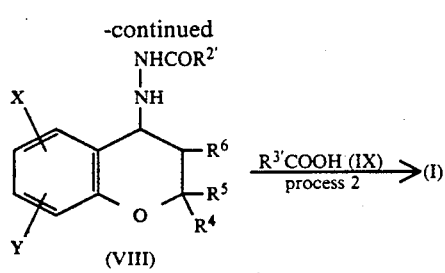

(VIII)

(in the reaction formulae, $R^{2'}$ and $R^{3'}$ represent respectively a group as defined above other than an alkylene having 1 to 2 carbon atoms which is combinedly together formed thereby and other symbols are all as defined above.)

This method is usable for the production of the compound of the general formula (I) wherein $R^2$ and $R^3$ are respectively a group as defined above other than an alkylene having 1 to 2 carbon atoms which is combinedly together formed thereby.

The reaction of process 1 can be conducted in an alcohol such as methanol or ethanol, if necessary, in the presence of triethylamine, pyridine or the like at room temperature or while heating, preferably while heating under reflux.

In the reaction of process 2, in the case where the compound of the general formula (IX) is a free carboxylic acid, the reaction can be conducted in an inert solvent in the presence of a condensing agent such as cyclohexylcarbodiimide, titanium tetrachloride, phosphorus halogenides (phosphorus trichloride, phosphorus oxychloride etc.), diethylchlorophosphite, o-phenylenechlorophosphite, ethyldichlorophosphite or the like under cooling, at room temperature or under heating. The reaction can be conducted by allowing a phosphorus halogenide in advance to act on the compound (VIII) in an inert solvent, followed by condensation with the compound (IX). For example, in the case where the phosphorus halogenide is phosphorus trichloride, about ⅓ mol phosphorus trichloride is in advance allowed to act on the compound (VIII) in an inert solvent in the presence of a tertiary base such as triethylamine, pyridine, N,N-dimethylaniline or the like under cooling or at room temperature, followed by the reaction with the compound (IX) at room temperature or while heating, preferably while heating under reflux.

In the case where an acid halide such as acid chloride or acid bromide, as a reactive derivative of the carboxylic acid of the general formula (IX), is used, the reaction can be conducted in an inert solvent in the presence of a tetiary base such as triethylamine, pyridine, N,N-dimethylaniline or the like under cooling or at room temperature, or in water in the presence of an alkali such as sodium hydroxide or potassium hydroxide under cooling or at room temperature.

In the case where an acid anhydride or a mixed acid anhydride such as an alkyl carbonate mixed acid anhydride, an alkyl phosphate mixed acid anhydride, an alkyl phosphite mixed acid anhydride, a mixed acid anhydride with sulfuric acid, as a reactive derivative of the compound (IX), is used, the reaction can be conducted in an inert solvent in the presence of a tertiary base such as triethylamine, pyridine, N,N-dimethylaniline or the like under cooling, at room temperature or under heating.

In the case where an active amide such as acid imidazolide, acid pyrrolidide or 2,4-dimethylpyrazolide, as a reactive derivative of the compound (IX), is used, the reaction can be conducted in an inert solvent at room temperature or under heating.

In the case where an active ester such as methyl ester, ethyl ester, p-nitrophenyl ester, p-chlorophenyl ester or the like, as a reactive derivative of the compound (IX), is used, the reaction can be conducted in an inert solvent at room temperature or while heating, preferably while heating under reflux.

As the inert solvents to be used in the above-mentioned condensation reactions, mention may be made of benzene, toluene, xylene, methanol, ethanol, isopropyl alcohol, ethyl ether, dioxane, tetrahydrofuran, chloroform, dichloromethane, dichloroethane, hexamethylphosphoricamide, diethylene glycol, dimethylformamide and the like and their mixed solvents. When the compound (IX) is a reactive derivative, the solvent can be suitably selected depending upon the species of the reaction derivative.

In general, preferably, the compound (IX) is an acid chloride, and the reaction is conducted in a solvent such as chloroform, methylenechloride or benzene in the presence of an organic base such as pyridine or triethylamine at 0°–50° C.

In this case, the compound of the general formula (I) wherein $R^6$ is a group as defined above other than hydroxyl group can be obtained by adjusting the amount ratio of the compound (IX) or the reactive derivative to be used and the reaction conditions.

METHOD 3

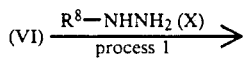

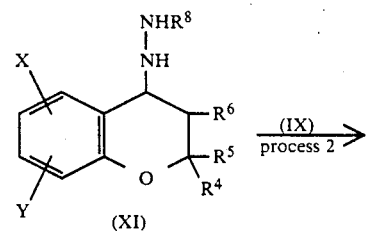

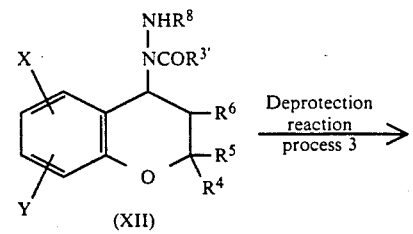

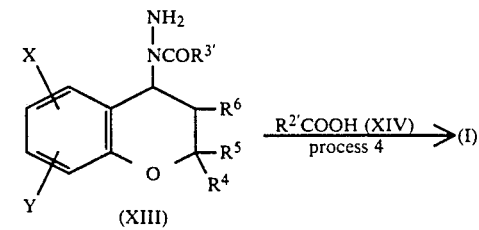

[in the above reaction formulae, $R^8$ represents an amino-protective group (benzyloxycarbonyl), tert-butoxycarbonyl, formyl, trityl, tosyl, etc.) and the other symbols are as defined above.]

This method is usable for the production of the compound of the general formula (I) wherein $R^2$ and $R^3$ are respectively a group as defined above other than an alkylene having 1 to 2 carbon atoms which is combinedly together formed thereby.

The reaction of process 1 can be conducted under the same conditions as those of process 1 of Method 2 mentioned above and the reactions of process 2 and process 4 can be conducted under the same conditions as those of process 2 of Method 2 mentioned above.

The deprotection reaction of process 3 can be conducted by conducting hydrogenolysis under ordinary pressure in ethanol or methanol with the use of palladium-carbon when $R^8$ is benzyloxycarbonyl and by allowing trifluoroacetic acid, hydrochloric acid-ethyl acetate or the like to act thereon when $R^8$ is a tert-butoxycarbonyl.

METHOD 4

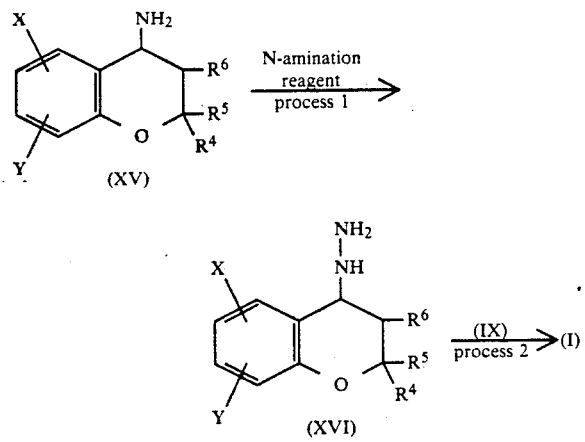

(in the above reaction formulae, each of the symbols is as defined above.)

This method is usable for the production of the compound of the general formula (I) wherein $R^2$ and $R^3$ are the same and as defined above except an alkylene which is combinedly together formed thereby.

The N-amination reaction of process 1 can be conducted in water at 0°–100° C., preferably in the presence of a small amount of gelatin when chloramine as a N-amination reagent is used and in an aqueous solution of potassium hydroxide or sodium hydroxide at room temperature to 100° C. when hydroxylamine-o-sulfonic acid as a N-amination reagent is used. In the method with cyclohexanespiro-3′-oxazilidine, in accordance with Synthesis pp. 529–533 (1988), N-amination reaction can be conducted by reacting in toluene at 80°–90° C. for 2–6 hours.

The reaction of process 2 can be conducted under the same conditions as those of process 2 of Method 2 as mentioned above.

METHOD 5

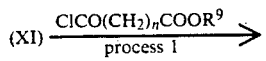

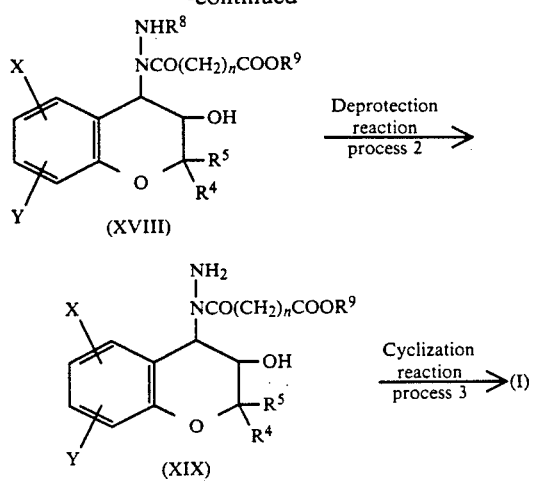

(in the above reaction formulae, $R^9$ represents a lower alkyl, n represents 1 or 2, and the other symbols are as defined above.)

This method is usable for the production of the compound of the general formula (I) wherein $R^2$ and $R^3$ combinedly together form an alkylene having 1 to 2 carbon atoms.

The reaction of process 1 can be conducted under the same conditions as those of process 2 of Method 2 as mentioned above and the reaction of process 2 can be conducted under the same conditions as those of process 3 of Method 3 as mentioned above.

The cyclization reaction of process 3 can be conducted by eliminating the alcohol ($R^9$OH) at pH higher than neutral range, if necessary, in the presence of an organic base such as pyridine, triethylamine or the like in ethanol, toluene, benzene or xylene while heating under reflux for 1–30 hours.

The compound of the general formula (I) wherein $R^6$ and $R^7$ combinedly together form a bond can be produced by treating the compound of the general formula (I) wherein $R^6$ is hydroxyl group and $R^7$ is hydrogen with a dehydrating agent (e.g. sulfuric acid, potassium sulfate, zinc chloride, phosphorus pentaoxide, phosphoric acid, metaphosphoric acid, boric anhydride, oxalic acid.)

The reaction can be conducted in the presence of a base (a hydroxide, a hydride or an amide of an alkali metal or an alkaline earth metal such as sodium hydroxide, potassium hydroxide, calcium hydroxide, sodium hydride, potassium hydride, calcium hydride, sodium amide or potassium amide, or an organic base such as triethylamine or pyridine) in a suitable inert solvent (e.g. alcohols such as methanol, ethanol, isopropanol, n-butanol and tert-butanol; ethers such as diethyl ether, diisopropyl ether, tetrahydrofuran and dioxane; glycol ethers such as ethylene glycol monomethyl ether, ethylene glycol monoethyl ether (methyl glycol or ethyl glycol) or ethylene glycol dimethyl ether (diglyme), ketons such as acetone or butanone; acetonitrile; nitrocompounds such as nitromethane and nitrobenzene; esters such as ethyl acetate; amides such as dimethylformamide (DMF), dimethylacetamide, and hexamethyl phosphoramide; sulfoxides such as dimethylsulfoxide (DMSO); halogenated hydrocarbons such as methylene dichloride, chloroform, trichloroethylene, 1,2-dichloroethane and carbon tetrachloride; hydrocarbons such as benzene, toluene and xylene and their mixed solvents).

blood pressures (mmHg) at the respective times are shown in Table 1.

TABLE 1

| Test Compound | Dosage (mg/kg, p.o.) | Blood pressure before administration (mmHg) | Lowered blood pressure after administration (Δ mmHg) | | | | | |
|---|---|---|---|---|---|---|---|---|
| | | | 1 hr. | 3 hrs. | 5 hrs. | 7 hrs. | 9 hrs. | 24 hrs. |
| Coumpound of Example 1 | 3 | 239 ± 5 | −39 ± 5 | −63 ± 7 | −65 ± 9 | −57 ± 12 | −64 ± 10 | −71 ± 7 |
| Compound of Example 2 | 1 | 233 ± 3 | −83 ± 7 | −75 ± 7 | −69 ± 9 | −64 ± 9 | −58 ± 9 | −25 ± 7 |
| Compound of Example 4 | 1 | 232 ± 4 | −47 ± 9 | −36 ± 3 | −42 ± 6 | −46 ± 10 | −47 ± 5 | −20 ± 5 |
| Compound of Example 19 | 3 | 223 ± 4 | −132 ± 3 | −121 ± 10 | −117 ± 7 | −102 ± 9 | NT | −28 ± 6 |
| Compound of Example 44 | 0.3 | 228 ± 10 | −151 ± 10 | −144 ± 7 | −134 ± 7 | −124 ± 11 | NT | −68 ± 26 |
| Control | 0 | 227 ± 6 | +7 ± 7 | +2 ± 4 | −1 ± 6 | +2 ± 4 | NT | +5 ± 4 |

In Table, NT designates "not measured".

For example, the reaction can be carried out by allowing sodium hydride to act thereon in dimethylsulfoxide at a temperature in the range from 0° C. to 150° C.

The compound of the general formula (I) wherein $R^6$ is a group other than hydroxyl group as defined above, can be produced by converting the corresponding compound of the general formula (I) wherein $R^6$ is hydroxyl group by the per se known acylation method.

Since the compounds of the present invention have at least one asymmetric carbon atom, there exist the optical isomers and stereoisomers due to the asymmetric carbon atom, which are encompassed in the present invention.

The thus obtained compounds of the general formula (I) can be separated from the reaction mixture and purified by a per se known method such as recrystallization or chromatography.

The compounds of the general formula (I) can be converted into their pharmaceutically acceptable salts by treating them with an inorganic acid (hydrochloric acid, hydrobromic acid, sulfuric acid, phosphoric acid, nitric acid etc.), or an organic acid (acetic acid, propionic acid, succinic acid, glycolic acid, lactic acid, malic acid, tartaric acid, citric acid, maleic acid, fumaric acid, methanesulfonic acid, p-toluenesulfonic acid, ascorbic acid etc.). Furthermore, they can be converted into their hydrates or various solvates.

Among the compounds of the present invention, the compounds having a chiral carbon atom as mentioned above are usually obtained as racemic bodies. Racemic bodies can be resolved into the optical isomers by the conventional methods. These optical isomers can also be produced by employing the optically active starting compounds. Individual diastereomers can be purified by fractional recrystallization or chromatography.

The antihypertensive actions of the compounds of the present invention are detailedly described by the following Pharmacological Experimental Examples.

PHARMACOLOGICAL EXPERIMENTAL EXAMPLE 1

Antihypertensive Action

Using six male spontaneously hypertensive rats per group (aged 20-24 weeks, weighing 350-420 g), the test compounds as suspended in a 0.5% methyl cellulose solution were orally administered and the blood pressures were measured by the tail cuff method with the use of systolic hemodynamometry apparatus (NARCO Corp. PE-300) 1, 3, 5, 7 and 24 hours later. The lowered

PHARMACOLOGICAL EXPERIMENTAL EXAMPLE 2

1. Effects on vertebral blood flow

Anesthesia was induced to mongrel dogs by intravenous injection of sodium pentobarbital (25 mg/kg, i.v.). The animals were ventilated artificially (20 ml/kg, 18 strokes/min) with inserted endotracheal tube. Vertebral blood flow was measured with electromagnetic flow meter (Nihon Kohden) at external circuration route made from the left common carotid artery to the right vertebral artery. Drugs were dissolved in saline or solvent (DMSO 9%, cremophor 2%, HCl or lactic acid) and injected intra-arterially. Results were expressed as the dose in μg, being equiactive to 100 μg papaverine.

2. Effects on coronary blood flow

Mongrel dogs were anesthetized and ventilated artificially. Coronary blood flow was measured with electromagnetic flow meter at external circuration route from the right femoral artery to the left coronary artery via the right common carotid artery used particular catheter. Drugs were injected intra-arterial injection. Results were expressed as the dose in μg, being equiactive to 3 μg nifedipine.

The results are shown in Table 2.

TABLE 2

| | Vertebral blood flow | Coronary blood flow | ratio |
|---|---|---|---|
| Compound of Example 2 | 13 | 1.4 | 9.3 |
| Compound of Example 19 | 18 | 1.4 | 13 |
| Compound of Example 44 | 38 | 1.7 | 22 |
| Compound of Example 59 | 4.7 | 0.5 | 9.4 |
| Compound of Example 60 | 19 | 3.0 | 6.3 |
| BRL-34915 | 16 | 3.3 | 4.8 |

PHARMACOLOGICAL EXPERIMENTAL EXAMPLE 3

Acute Toxicity

The compounds of Examples 1 and 2 of the present invention were orally administered to male mice at the dosage of 1000 mg/kg, and no death occurrences were observed.

As is clear from the foregoing Pharmacological Experimental Examples and various pharmacological experiments, the compounds of the present invention and their pharmaceutically acceptable salts exhibit remarkable and durable antihypertensive actions and peripheral vascular relaxant actions, and therefore are useful as the therapeutic medicines for hypertensives.

They also display selective coronary vasodilating actions and the actions are of extremely long-lasting, and thus of use as therapeutic medicines for cardiovascular disturbances such as angina pectoris and cardiac insufficiency.

Besides, since they exhibit relaxant actions on vascular smooth muscles and the other vascular muscles due to the above-mentioned actions, they are useful as therapeutic medicines for digestive tract ulsers, sensitive intestinal syndromes, diverticulum diseases, reversible bronchial obstruction and asthma, premature delivery, incontinence, cerebral vascular diseases, loss of hairs and baldness.

When the compounds of the present invention and their pharmaceutically acceptable salts are used as pharmaceuticals, they are usually admixed with pharmaceutically acceptable additives such as carriers, vehicles, diluents and anxiliary solubilizers and can be orally or parenterally safely administered in the forms such as tablets (including sugar coated tablets and film-coated tablets), capsules, powders, granules, injections, instillations, suppositories and cataplasms. While the dosage may varies depending on sex, age, body weight, symptoms and the like of the patients, daily dosage per an adult man is usually, in the case of oral administration, in the range from about 1 to 500 mg, at one time dose or at several divided doses.

PHARMACEUTICAL FORMULATION EXAMPLE

Tablets containing 0.25 mg per tablet of the compound of the present invention can be produced in accordance with the following composition.

| | |
|---|---|
| Compound of Example 2 | 0.25 mg |
| Lactose | 68.5 mg |
| Corn starch | 25.0 mg |
| Crystalline cellulose | 20.0 mg |
| Polyvinylpyrrolidone K-30 | 2.0 mg |
| Talc | 4.0 mg |
| Magnesium stearate | 0.25 mg |
| | 120.0 mg |

The compound of Example 2 was pulverlized into fine powders of mean particle diameter of not less than 10 μ. Said compound, lactose, corn starch and crystalline cellulose were mixed thoroughly in a kneading machine, and then a paste of polyvinylpyrrolidone was added thereto. The mixture was kneaded. The kneaded mixture was heat-dried at 50° C. into those of a water-content in the range of 3–4% and subjected to sieve of 24 mesh. The thus obtained kneaded powders were mixed sufficiently with magnesium stearate and talc. Thereafter, tablets were prepared by the conventional method.

The invention will be described hereinbelow in more detail by way of reference examples and examples, but is not meant to be limited to them.

REFERENCE EXAMPLE 1

A 6.9 g quantity of 6-cyano-3,4-epoxy-3,4-dihydro-2,2-dimethyl-2H-1benzopyran and 6.3 g of o-benzylhydroxylamine. hydrochloride were dissolved in 30 ml of ethanol. To the solution, 6.7 ml of triethylamine was added, and the mixture was heated under reflux for 18 hours. After the completion of the reaction, the solution was vacuum concentrated, and to the residue were added water and ethyl acetate, and the resulting solution was shaken. After its organic layer was washed with an aqueous sodium chloride solution twice, it was filtered and the filtrate was vacuum concentrated. Crude trans-4-(N-benzyloxy)amino-6-cyano-3,4-dihydro-2,2-dimethyl-2H-1-benzopyran-3-ol (11.9 g) was thus obtained as an oleaginous product. This product may be used as such, but can be purified in the following manner, if necessary.

The crude product, 5.0 g, was column chromatographed on 165 g of silica gel (Merck 60) by passing an elution solvent (chloroform: ethyl acetate=20:1), and the intended fraction was concentrated to yield 3.6 g of an oleaginous product. A portion of this product was dissolved in ethanol, a slight amount of conc. hydrochloric acid was added, and the solution was recrystallized from ethyl acetate to give white crystals of its hydrochloride, m.p. 177°–178° C. (decomposition).

REFERENCE EXAMPLE 2

6-Cyano-3,4-epoxy-3,4-dihydro-2,2-dimethyl-2H-1-benzopyran (5.0 g) and 4.0 g of acetohydrazide were dissolved in 20 ml of ethanol and the solution was heated under reflux for 9 hours. After the reaction, the ethanol was distilled off under reduced pressure and the residue was crushed by adding ice water and filtered to obtain crystals. The crystals were dried and recrystallized from ethyl acetate-ethanol (7:1) to give 5.3 g of trans-4-(2-acetylhydrazino)-6-cyano-3,4-dihydro-2,2-dimethyl-2H-1-benzopyran-3-ol as white crystals, m.p. 209°–210° C.

REFERENCE EXAMPLE 3

The procedure of Reference Example 2 was repeated except that 1.3 g of 6-cyano-3,4-epoxy-3,4-dihydro-2,2-dimethyl-2H-1-benzopyran and 1.0 g of benzoylhydrazine was used, and 1.18 g of trans-4-(2-benzoylhydrazino)-6-cyano-3,4-dihydro-2,2-dimethyl-2H-1-benzopyran-3-ol was obtained as white crystals, m.p. 197°–199° C. (recrystallized from hexane-ethanol).

REFERENCE EXAMPLE 4

A similar procedure to Reference Example 2 was performed by using 6-cyano-3,4-epoxy-3,4-dihydro-2,2-dimethyl-2H-1benzopyran semicarbazide.hydrochloride and triethylamine, and yielded trans-4-(2-carbamoylhydrazino)-6-cyano-3,4-dihydro2,2-dimethyl-2H-1-benzopyran-3-ol, m.p. 217°–218° C. (decomposition) (recrystallized from ethyl acetate-ethanol).

REFERENCE EXAMPLE 5

6-Cyano-3,4-epoxy-3,4-dihydro-2,2-dimethyl-2H-1-benzopyran (8.0 g) and tert-butyl carbazate (6.3 g) were dissolved in 40 ml of ethanol and the solution was heated under reflux for 28 hours. The resulting ethanol was distilled off and the residue was recrystallized from 80 ml of hexane and 8 ml of ethanol to yield 8.7 g of trans-4-(2-tert-butoxycarbonyl- hydrazino)-6-cyano-3,4-dihydro-2,2-dimethyl-2H-1-benzopyran-3-ol as white crystals, m.p. 136°–138° C.

REFERENCE EXAMPLE 6

A similar procedure to Reference Example 5 was performed by using 6-cyano-3,4-epoxy-3,4-dihydro-2,2-dimethyl-2H-1-benzopyran and methylcarbazate, and as a result, trans-6-cyano-3,4-dihydro-2,2-dimethyl-4-(2-methoxycarbonylhydrazine)-2H-1-benzopyran-3-ol was obtained, m.p. 174°-175° C. (recrystallized from hexane-ethyl acetate).

EXAMPLE 1

The crude produce, [trans-4(N-benzyloxy)amino-6-cyano-3,4-dihydro-2,2-dimethyl-2H-1-benzopyran-3-ol], (11.6 g) obtained in Reference Example 1 was dissolved in 50 ml of chloroform, and 13 ml of pyridine was added. To the solution was added portionwise with stirring under ice cooling 4.0 ml of acetyl chloride, and the resulting mixture was stirred under ice cooling for 40 minutes and vacuum concentrated. To the residue thus obtained, water and ethyl acetate were added, and the solution was shaken for partitioning. The organic layer separated was washed with an aqueous sodium chloride solution and concentrated. The crystalline residue was recrystallized from ethanol to give 7.5 g of trans-4-(N-acetyl-N-benzyloxy)amino-6-cyano-3,4-dihydro-2,2-dimethyl-2H-1benzopyran-3-ol as white crystals, m.p. 177.5°-179° C.

EXAMPLE 2

The compound of Example 1 (6.8 g) was dissolved in 150 ml of ethanol, and a dispersion of 1.8 g of 10% palladium carbon in 10 ml of water was added. The mixture was subjected to hydrogenolysis under normal pressure while stirring on a water bath at 35° C.

After confirming the consumption and dissipation of the starting material by thin layer chromatography, the palladium carbon was filtered off and the filtrate was vacuum concentrated to yield trans-4-(N-acetyl-N-hydroxy)amine-6-cyano-3,4-dihydro-2,2-dimethyl-2H-1-benzopyran-3-ol as a glassy amorphous solid. Further when recrystallized from ethyl acetate, it gave 5.1 g of white crystals of a solvation product with about 1/6 ethyl acetate, m.p. 108°-113° C. (decomposed).

EXAMPLE 3

The compound of Example 2 (glassy amorphous solid), 530 mg, was dissolved in a mixture of 10 ml of methanol and 5 ml of water, to which solution 1.5 g of anhydrous potassium carbonate and 1.5 ml of methyl iodide were added, and the mixture was stirred on a water bath at 30°-35° C. for 135 minutes and vacuum concentrated. To the residue, water and ethyl acetate were added and the solution was shaken. The resulting organic layer was washed with water and filtered and concentrated. The residue was an amorphous glassy product and, when washed with hexane, afforded 430 mg of powders of trans-4-(N-acetyl-N-methoxy)amino-6-cyano-3,4-dihydro-2,2-dimethyl-2-H-1-benzopyran-3ol.

NMR($d_6$—DMSO) δ: 1.15 (3H, s), 1.44 (3H, s), 2.21 (3H, s), 3.62 (3H, s), 3.94 (1H, g), 5.16 (1H, d) 5.83 (1H, d), 6.90 (1H, d), 7.43 (1H, s), 7.57 (1H, d).

EXAMPLE 4

The product of Example 2 (glassy amorphous solid), 1.74 g, was dispersed in 18 ml of chloroform, and then 7.0 ml of acetic anhydride was added. The mixture was stirred on a water bath at 40°-50° C. for 20 hours. After the completion, the overall solvent was completely distilled off under reduced pressure and the residue was vacuum dried in a desiccator holding potassium hydroxide to give 2.0 g of crude trans-4-(N-acetyl-N-acetyloxy)amino-6-cyano-3,4-dihydro-2,2-dimethyl-H-1-benzopyran-3-ol in an amorphous glassy state. This yielded, when recrystallized from a mixture solvent of hexane-ethyl acetate-ethanol, 1.3 g of the purified product as white crystals, m.p. 144.5°-146° C.

EXAMPLE 5

A similar procedure to Example 1 was performed by using 670 mg of the crude product obtained in Reference Example 1 and 0.73 ml of propionyl chloride. The resulting solution was column chromatographed on silica gel (elution solvent: chloroform-ethyl acetate (5:1)) and concentrated to give 620 mg of trans-4-(N-benzyloxy-N-propionyl)amino-6-cyano-3,4-dihydro-2,2-dimethyl 2H-1-benzopyran-3-ol, m.p. 142.5°-144.5° C.

EXAMPLE 6

A similar procedure to Example 2 was performed by using 720 mg of the compound of Example 5 and yielded 510 mg of trans-4-(N-hydroxy-N-propionyl)amino-6-cyano-3,4-dihydro-2,2-dimethyl-2H-1-benzopyran-3-ol as amorphous powders.

NMR ($d_6$—DMSO) δ: 1.08 (3H, t), 1.18 (3H, s), 1.44 (3H, s), 2.55 (2H, q), 3.84 (1H, q), about 5.45 (2H, m), 6.89 (1H, d), 7.28 (1H, s), 7.56 (1H, d), 9.40 (1H, broad s).

EXAMPLE 7

2-Furan carboxylic acid, 400 mg, was suspended in 6 ml of chloroform and 0.9 ml of thionyl chloride was added. The mixture was heated under reflux for 100 minutes and the solvent was distilled off under reduced pressure. The residue was dissolved in 4 ml of chloroform and the solution was added to a mixture solution consisting of 800 mg of the crude product of Reference Example 1, 1 ml of pyridine and 4 ml of chloroform with stirring at room temperature, and the mixture was further stirred at 35° C. for 90 minutes. The reaction solution was concentrated under reduced pressure. To the residue were added water and ethyl acetate. The solution was shaken, and the organic layer separated was washed with a dilute aqueous solution of potassium carbonate and then with an aqueous sodium chloride solution, and subsequently vacuum concentrated. The residue was dissolved in 10 ml of methanol, and then, 5 ml of 1N sodium hydroxide solution was added. After the solution had been stirred at room temperature for 3 hours and concentrated, the resulting residue was extracted with ethyl acetate. The solvent was distilled off and the resulting residue, when recrystallized from hexane-ethyl acetate, afforded 410 mg of trans-6-cyano3,4-dihydro-2,2-dimethyl-4-[N-(2-furoyl)-N-benzyloxy]amino2H-1-benzopyran-3-ol. This product, 630 mg, was dissolved in 20 ml of ethanol and then, 250 mg of 10palladium carbon was added. The mixture was subjected to reaction and treatment in a similar procedure to Example 2 at a reaction temperature of 30°-35° C. The concentrated residue, when recrystallized from hexane-ethanol, gave 450 mg of trans-6-cyano-3,4-dihydro2,2-dimethyl-4-[N-(2-furoyl)-N-hydroxy]amino-2H-1-benzopyran3-ol, m.p. 117°-121° C. (decomposition).

EXAMPLE 8

A similar procedure to Example 7 was conducted by using 760 mg of the purified product of Reference Example 1 and 0.41 ml of benzoyl chloride to result in the concentrated residue. When recrystallized from hexane-ethanol, it gave 710 mg of trans-4-(N-benzoyl-N-benzyloxy)amino-6-cyano-3,4-dihydro-2,2-dimethyl-2H-1-benzopyran-3-ol as white crystals, m.p. 206.5°–207° C.

EXAMPLE 9

Normal-pressure hydrogenolysis and treatment were performed in a similar procedure to Example 2 by using 900 mg of the compound of Example 8 and 300 mg of 10% palladium carbon, and thus, 680 mg of trans-4-(N-benzoyl-N-hydroxy)amino-6-cyano-3,4-dihydro-2,2-dimethyl-2H-1-benzopyran-3-ol in amorphous white powders was obtained.

NMR (CDCl$_3$) δ: 1.05 (3H, s), 1.72 (3H, s), 4.21 (1H, d),
4.52 (1H, broad s), 4.97 (1H, broad d), 6.83 (1H, d), 7.3–7.7 (7H, m).

EXAMPLE 10

The crude product of Reference Example 1, 1940 mg, was dissolved in a mixture of 8 ml of chloroform and 1.3 ml of pyridine, and 0.80 ml of ethyl chloroformate was added with stirring at room temperature. Thereafter, the mixture was stirred at room temperature for 20 minutes. The solvent was distilled off and to the residue was added water. After extraction with ethyl acetate, the organic layer was washed with an aqueous solution of sodium chloride and filtered. The filtrate was concentrated and the resulting residue was recrystallized from hexane-ethanol to give 1440 mg of trans-4-(N-benzyloxy-N-ethoxycarbonyl)amino-6-cyano-3,4-dihydro2,2-dimethyl-2H-1-benzopyran-3-ol as white crystals, m.p. 143°–144.5° C.

EXAMPLE 11

A normal pressure hydrogenolysis and treatment were conducted in a similar procedure to Example 2 by using 1360 mg of the compound of Example 10 and 400 mg of 10% palladium carbon and thereafter, the concentrated residue was recrystallized from hexane-ethyl acetate to afford 900 mg of trans-4-(N-hydroxy-N-ethoxycarbonyl)amino-6-cyano-3,4-dihydro-2,2-dimethyl-2H-1-benzopyran-3-ol as white crystals, m.p. 181°–184° C. (decomposition).

EXAMPLE 12

The crude product of Reference Example 1, 1.76 g, was dissolved in a mixture solution of 4 ml of acetic acid and 5 ml of water, and to this was added, with vigorous stirring at room temperature, 2.0 g of sodium cyanate in several divided portions. The mixture was stirred at room temperature for about 150 minutes and allowed to stand overnight. After addition of ice water, the deposited gum-like product was separated by decantation and sufficiently dried under diminished pressure in a desiccator. When recrystallized from ethanol-hexane, it afforded 700 mg of trans-4-(N-benzyloxy-N-carbamoyl)amino-6-cyano-3,4-dihydro-2,2-dimethyl-2H-1-benzopyran-3-ol, m.p. 179°–181° C.

EXAMPLE 13

A normal-pressure hydrogenolyis and treatment similar to Example 2 were effected by using 1030 mg of the compound of Example 12 and 300 mg of 10% palladium carbon, and the resulting amorphous glassy product was column chromatographed on 27 g of silica gel (Merck 60) in an elution solvent of chloroform-methanol (8:1). The main fractions were collected and concentrated. The resulting product in amorphous powders was further washed with a chloroform-hexane mixture and filtered. After drying, 440 mg of trans-4-(N-carbamoyl-N-hydroxy)amino-6-cyano-3,4-dihydro-2,2-dimethyl-2H-1-benzo-pyran-3-ol was obtained.

NMR (d$_6$—DMSO) δ: 1.16 (3H, s), 1.42 (3H, s), 3.80 (1H, q),
5.15 (1H, d), 5.35 (1H, d), 6.49 (2H, s), 6.88 (1H, d), 7.39 (1H, s), 7.55 (1H, d), 9.11 (1H, s).

EXAMPLE 14

The crude product of Reference Example 1, 1740 mg, was dissolved in 7 ml of chloroform and to this was added 1.1 ml of methyl isocyanate at room temperature. The mixture was stirred on a water bath at 40°–45° C. for 4 hours. The solvent was distilled off under reduced pressure and the residue was recrystallized from hexane-ethyl acetate to yield 1220 mg of trans-4-[N-benzyloxy-N-(N-methylcarbamoyl)]amino-6-cyano-3,4-dihydro-2,2-dimethyl-2H-1-benzopyran-3-ol as white crystals, m.p. 154°–155.5° C. (sintered from 144° C).

EXAMPLE 15

A normal pressure hydrogenolysis and treatment were performed in a similar procedure to Example 2 by using 1090 mg of the compound of Example 14 and 290 mg of 10% palladium carbon, and yielded 750 mg of trans-4-[N-hydroxy-N-(N-methylcarbamoyl)]amino-6-cyano-3,4-dihydro-2,2-dimethyl-2H-1-benzopyran-3-ol as amorphous white solid.

NMR (d$_6$—DMSO) δ: 1.16 (3H, s), 1.43 (3H, s), 2.70 (3H, d),
3.82 (1H, q), 5.13 (1H, d), 5.34 (1H, d), 6.88 (1H, d), 6.98 (1H, d), 7.40 (1H, s), 7.55 (1H, d), 9.00 (1H, broad s).

EXAMPLE 16

The crude product of Reference Example 1, 1100 mg, was dissolved in 7.0 ml (99%) of formic acid and to this was added 0.52 ml of acetic anhydride. The mixture was stirred at room temperature for 100 minutes. The solvent was completely distilled off under reduced pressure, and the residue was dried in a vacuum desiccator. Then, when recrystallized from hexane-ethyl acetate (4:1), it yielded 770 mg of trans-4-(N-benzyloxy-N-formyl)amino-6-cyano-3,4-dihydro-2,2-dimethyl2H-1-benzopyran-3-ol as white crystals, m.p. 140°–142° C.

EXAMPLE 17

A hydrogenolysis was performed in a similar procedure to Example 2 by using 830 mg of the compound of Example 16 dissolved in 25 ml of ethanol and 200 mg of 10% palladium carbon. As a result, 540 mg of trans-6-cyano-3,4-dihydro2,2-dimethyl-4-(N-formyl-N-hydroxy)amino-2H-1-benzopyran-3-ol in amorphous powders was obtained.

NMR (d$_6$—DMSO) δ: 1.16 (3H, s), 1.44 (3H, s), 3.75 (1H, m),
4.72 (1H, d), 5.90 (1H, d), 6.92 (1H, d), 7.51 (1H, s), 7.60 (1H, d), 8.17 (1H, s), 9.20 (1H, broad s).

EXAMPLE 18

The crude product of Reference Example 1, 3.09 g, was dissolved in 6 ml of chloroform and to this was added 5 ml of pyridine. While stirring under ice cooling, a suspension of 3.6 g of 3-nicotinic acid chloride hydrochloride in 6 ml of chloroform, in two divided portions, was added to it and the mixture was stirred at 40° C. for 4 hours. The solvent was distilled off under reduced pressure and the residue was dissolved in 10 ml of methanol. A solution of 2.1 g of sodium hydroxide in 8 ml of water was added thereto and the mixture was stirred at room temperature for 35 minutes and subsequently concentrated. To the residue, warm water was added, and the solution was extracted with ethyl acetate. The organic layer was washed with a dilute aqueous solution of potassium carbonate and with an aqueous solution of sodium chloride in sequence, partitioned, treated with activated charcoal, and concentrated under reduced pressure. The residue was recrystallized from ethanol-hexane (3:2) to give 1.75 g of trans-4-(N-benzyloxy-N-nicotinoyl)amino-6-cyano3,4-dihydro-2,2-dimethyl-2H-1-benzopyran-3-ol, m.p. 191°–192.5° C.

EXAMPLE 19

A hydrogenolysis was performed in a similar manner to Example 2 by using 1.59 g of the compound of Example 18 suspended in 34 ml of ethanol and 0.45 g of 10% palladium carbon, and the product thus obtained was recrystallized from ethanol-hexane (2:1) to give 1.05 g of trans-6-cyano-3,4-dihydro-2,2-dimethyl-4-(N-hydroxy-N-nicotinoyl)amino-2H-1-benzopyran-3-ol, m.p. 205.5°–206.5° C. (decomposition).

EXAMPLE 20

(1) The crude product of Reference Example 1, 3300 mg, was dissolved in 11 ml of chloroform, and to this was added 3.3 ml of pyridine. Under ice cooling, a solution of 3040 mg of N-phthaloylglycine chloride in 15 ml of chloroform was added, and the mixture was stirred at room temperature for 30 minutes and further at 40° C. for 75 minutes. After vacuum concentration, water and ethyl acetate were added and shaken, and the partitioned organic layer was washed with an aqueous sodium bicarbonate solution and an aqueous sodium chloride solution, and concentrated. The residue was recrystallized from hexane-ethyl acetate (4:3) to yield 2690 mg of N-benzyloxy-N-phthaloylaminoacetyl compound, m.p. 183.5°–85° C.

(2) The compound obtained in (1) above, 2360 mg, was dissolved in 10 ml of methanol, 0.35 ml of 100% hydrazine hydrate was added, and the mixture was stirred overnight and further at 45° C. for 2 hours. The methanol was distilled off under reduced pressure. To the residue, ethyl acetate was added and the solution was stirred. After undissolved portion had been filtered off, the filtrate was concentrated and the residue obtained was purified by silica gel column chromatography (eluted with a chloroform-methanol (8:1)) to give 1520 mg of trans-4-(N-aminoacetyl-N-benzyloxy)amino-6-cyano-3,4-dihydro-2,2-dimethyl-2H-1-benzopyran-3-ol as an amorphous glassy product.

NMR (d$_6$—DMSO) δ: 1.20 (3H, s), 1.45 (3H, s), 1.73 (2H, broad
s), 3.75 (2H, s), 4.07 (1H, s), 4.95 (2H, d), 5.93 (1H, s), 6.95 (1H, d), 7.25 - 7.35 (5H, m), 7.55 (1H, s), 7.60 (1H, d).

EXAMPLE 21

The compound of Example 20, 1250 mg, was dissolved in 25 ml of ethanol and subjected to debenzylation with 310 mg of 10% palladium carbon in a similar manner to Example 2. After concentration, to the resulting residue was added an ethyl acetate-hexane (2:1) mixture, and the solution was stirred, filtered, and dried. Thus, 850 mg of trans-4-(N-aminoacetyl-N-hydroxy)amino-6-cyano-3,4-dihydro-2,2-dimethyl-2H-1-benzo-pyran-3-ol in pale yellow amorphous powders was obtained.

NMR (d$_6$—DMSO) δ: 1.21 (3H, s), 1.47 (3H, s), 3.80–4.25 (3H,
m), 5.36 (1H, d), 5.82 (1H, d), 6.95 (1H, d), 7.23 (1H, s), 7.62 (1H, d), 8.18 (2H, s), 10.30 (1H, s).

EXAMPLE 22

The crude product obtained in Reference Example 1 and methoxyacetyl chloride were allowed to react in a similar procedure to Example 7 and the resulting crude product was purified by silica gel column chromatography, whereby trans-4-(N-benzyloxy-N-methoxyacetyl-)amino-6-cyano-3,4-dihydro-2,2-dimethyl-2H-1-benzo-pyran-3-ol was obtained as white crystals, m.p. 140°–143° C. (recrystallized from hexane-ethyl acetate (5:1)).

EXAMPLE 23

The compound of Example 22 was subjected to debenzylation in a similar manner to Example 2 to yield trans-6-cyano-3,4-dihydro-2,2-dimethyl-4-(N-hydroxy-N-methoxyacetyl)amino-2H-1-benzopyran-3-ol as white crystals, m.p. 192°–193° C. (decomposed) (recrystallized from hexane-ethyl acetate (2:1)).

EXAMPLE 24

The compound of Example 7,570 mg, was dissolved in 5 ml of chloroform and to this were added at room temperature 250 mg of benzoyl chloride and 0.3 ml of triethylamine. The mixture was stirred for 15 minutes and the solvent was distilled off under reduced pressure. To the residue was added ice water and the solution was extracted with ethyl acetate. The organic layer was washed with an aqueous sodium chloride solution and concentrated. When recrystallized from hexaneethyl acetate (2:1), this yielded 570 mg of trans-4-[N-benzoyloxy-N-(2-furoyl)]amino-6-cyano-3,4-dihydro-2,2-dimethyl2H-1-benzopyran-3-ol as white crystals, m.p. 182°–183° C.

EXAMPLE 25

(1) (-)-6-Cyano-3,4-dihydro-2,2-dimethyl-3,4-epoxy-2H-1benzopyran (2.0 g) and 1.6 g of o-benzylhydroxylamine.hydrochloride were dissolved in 8.0 ml of ethanol and to this was added 1.5 ml of triethylamine. The mixture was heated under reflux for 28 hours and the solvent was distilled off under reduced pressure. To the residue was added water, and the solution was extracted with ethyl acetate. The organic layer was washed with an aqueous solution of sodium chloride and filtered. The filtrate was concentrated to give 3.5 g of (+)-(3S,4R)-trans-4-(N-benzyloxy)amino-6-cyano-3,4-dihydro2,2-dimethyl-2H-1-benzopyran-3-ol as a brown sticky, oleaginous product. This compound is to be used in the following reaction without purification.

(2) (+)-(3S,4R)-Trans-4-(N-benzyloxy)amino-6-cyano-3,4-dihydro-2,2-dimethyl-2H-1-benzopyran-3-ol, 3.3 g obtained in (1) above was dissolved in 30 ml of chloroform, and 2.3 g of pyridine was added to this. While stirring under ice cooling, 1.1 g of acetyl chloride was added dropwise, and stirring was continued at room temperature for 90 minutes. Then, the mixture was washed with a dilute hydrochloric acid, an aqueous solution of sodium chloride, and water, in this sequence, and dried. The solvent was distilled off and the residue obtained was recrystallized from ethanol twice to give 2.0 g of (+)-(3S,4R)-trans-4-(N-acetyl-N-benzyloxy)amino-6-cyano3,4-dihydro-2,2-dimethyl-2H-1-benzopyran-3-ol as white crystals, m.p. 145°–147° C, $[\alpha]_D^{24} = +48.0°$ (C=1, CHCl$_3$).

EXAMPLE 26

A 3.7 g quantity of (+)-(3S,4R)-trans-4-(N-acetyl-N-benzyloxy)amino-6-cyano-3,4-dihydro-2,2-dimethyl-2H-1-benzopyran-3-ol was dissolved in 30 ml of ethanol while heating and to this was added 0.61 g of 5% palladium carbon. The solution was subjected to hydrogenolysis for 70 minutes under heating at 30°–40° C. while admitting hydrogen gas thereto. The reaction was followed by thin layer chromatography and completed by confirming that the starting materials were consumed and dissipated. The palladium carbon was filtered out of the reaction mixture and the filtrate was concentrated. The residue was recrystallized from hexane-ethyl acetate twice to yield 2.85 g of (−)-(3S,4R)-trans-4-(N-acetyl-N-hydroxy)amino-6-cyano-3,4-dihydro-2,2-dimethyl-2H-1-benzopyran-3-ol as white fine powder crystals, m.p. 154°–157° C., $[\alpha]_D^{23} = -75.6°$ (C=1, CHCl$_3$).

EXAMPLE 27

(1) (+)-6-Cyano-3,4-epoxy-3,4-dihydro-2,2-dimethyl-2H-1-benzopyran-3-ol and o-benzylhydroxylamine.hydrochloride were made to react in a similar procedure of Example 25(1) thereby to yield (-)-(3R,4S)-trans-4-(N-benzyloxy)amino-6-cyano-3,4-dihydro-2,2-dimethyl-2H-1-benzopyran-3-ol.

(2) Then, this compound and acetyl chloride were made to react in a similar procedure to Example 25(2) and the product, when recrystallized from ethanol, yielded (−)-(3R,4S)-trans-4-(N-acetyl-N-benzyloxy)amino-6-cyano-3,4-dihydro-2,2-di-methyl-2H-1-benzopyran-3-ol, m.p. 147°–149° C., $[\alpha]_D^{23} = -47.5°$ (C=1, CHCl$_3$).

EXAMPLE 28

(−)-(3R,4S)-Trans-4-(N-acetyl-N-benzyloxy)amino-6-cyano-3,4-dihydro-2,2-dimethyl-2H-1-benzopyran-3-ol obtained in Example 27 was subjected to hydrogenolysis and recrystallization from hexane-ethyl acetate in a similar procedure to Example 26, and (+)-(3R,4S)-trans-4-(N-acetyl-N-hydroxy)-amino-6-cyano-3,4-dihydro-2,2-dimethyl-2H-1-benzopyran-3-ol was obtained, m.p. 158°–161° C., $[\alpha]_D^{23} = +79.3°$ (C=1, CHCl$_3$).

EXAMPLE 29

(+)-(3S,4R)-Trans-4-(N-benzyloxy)amino-6-cyano-3,4-dihydro-2,2-dimethyl-2H-1-benzopyran-3-ol obtained in Example 25(1) and 3-nicotinic acid chloride.hydrochloride were made to react in a similar procedure to Example 25(2), and by recrystallization from ethanol-hexane (2:1), (+)-(3S,4R)-trans-4-(N-benzyloxy-N-nicotinoyl)amino-6-cyano-3,4-dihydro-2,2-dimethyl-2H-1-benzopyran-3-ol was obtained, m.p. 204°–206° C., $[\alpha]_D^{23} = +29.8°$ (C=1, CHCl$_3$).

EXAMPLE 30

(+)-(3S,4R)-Trans-4-(N-benzyloxy-N-nicotinoyl)amino-6-cyano-3,4-dihydro-2,2-dimethyl-2H-1-benzopyran-3-ol obtained in Example 29 was subjected to hydrogenolysis in a similar procedure to Example 26 and the product was recrystallized from hexane-ethanol (2:1) to yield (-)-(3S,4R)-trans-6-cyano-3,4-dihydro-2,2-dimethyl-4-(N-hydroxy-N-nicotinoyl)-amino-2H-1-benzopyran-3-ol, m.p. 180°–183° C. (decomposition), $[\alpha]_D^{24} = -23.6°$ (C=1, CHCl$_3$).

EXAMPLE 31

(−)-(3R,4S)-Trans-4-(N-benzyloxy)amino-6-cyano-3,4-di-hydro-2,2-dimethyl-2H-1-benzopyran-3-ol obtained in Example 27(1) and 3-nicotinic acid chloride.hydrochloride were made to react in a similar procedure to Example 25(2), and by recrystallization from ethanol-hexane (2:1), (−)-(3R,4S)-trans-4-(N-benzyloxy-N-nicotinoyl)amino-6-cyano-3,4-dihydro2,2-dimethyl-2H-1-benzopyran-3-ol was obtained, m.p. 206°–208° C., $[\alpha]_D^{23} = -27.9°$ (C=1, CHCl$_3$).

EXAMPLE 32

(−)-(3R,4S)-Trans-4-(N-benzyloxy-N-nicotinoyl)amino-6-cyano-3,4-dihydro-2,2-dimethyl-2H-1-benzopyran-3-ol obtained in Example 31 was subjected to hydrogenolysis in a similar procedure to Example 26, and the product was recrystallized from hexane-ethanol (2:1) to give (+)-(3R,4S)-trans-6-cyano-3,4-dihydro-2,2-dimethyl-4-(N-hydroxy-N-nicotinoyl)-amino-2H-1-benzopyran-3-ol, m.p. 178°–181° C. (decomposition), $[\alpha]_D^{24} = +25.2°$ (C=1, CHCl$_3$).

The following compounds were likewise obtained in a similar manner to the foregoing examples:

EXAMPLE 33

Trans-4-(N-acetyl-N-benzyloxy)amino-3,4-dihydro-2,2-dimethyl-6-nitro-2H-1-benzopyran-3-ol, m.p. 178°–181° C. (recrystallized from chloroform-hexane).

EXAMPLE 34

Trans 4-(N-acetyl-N-hydroxy)amino-3,4-dihydro-2,2-dimethyl6-nitro-2H-1-benzopyran-3-ol, m.p. 195.5°–196° C. (decomposition) (recrystallized from ethyl acetate-hexane (2:1)).

EXAMPLE 35

Trans-4-(N-acetyl-N-benzyloxy)amino-6-chloro-3,4-dihydro2,2-dimethyl-2H-1-benzopyran-3-ol, m.p. 129°–132° C. (recrystallized from isopropyl ether-petroleum ether).

EXAMPLE 36

Trans-4-(N-acetyl N-hydroxy)amino-6-chloro-3,4-dihydro2,2-dimethyl-2H-1-benzopyran 3-ol in amorphous powder.

NMR (d$_6$—DMSO) δ: 1.12 (3H, s), 1.40 (3H, s), 2.13 (3H, s),
3.83 (1H, d), 5.36 (1H, d), 6.75 (1H, m), 6.89 (1H, s),
7.14 (1H, q), 9.55 (1H, broad s).

EXAMPLE 37

Trans-4-[N-acetyloxy-N-(2-furoyl)]amino-6-cyano-3,4-dihydro-2,2-dimethyl-2H-1-benzopyran-3-ol, m.p.

198°-200° C. (sintered from the vicinity of 150° C.), (recrystallized from hexane-ethyl acetate (1:1)).

EXAMPLE 38

Trans-4-(N-acetyloxy-N-benzoyl)amino-6-cyano-3,4-dihydro2,2-dimethyl-2H-1-benzopyran-3-ol, m.p. 160°-162° C. (recrystallized from hexane-ethyl acetate (1:1)).

EXAMPLE 39

Trans-4-(N-benzoyl-N-benzoyloxy)amino-6-cyano-3,4-dihydro2,2 dimethyl 2H-1-benzopyran-3-ol, m.p. 185°-186° C. (recrystallized from hexane-ethyl acetate (2:1)).

EXAMPLE 40

Trans-4-(N-benzoyloxy-N-nicotinoyl)amino-6-cyano-3,4-dihydro-2,2-dimethyl-2H-1-benzopyran-3-ol, m.p. 190.5°-192° C. (recrystallized from hexane-ethyl acetate (10:1)).

EXAMPLE 41

Trans-4-(N-benzyloxy-N-pentafluoropropionyl)amino-6-cyano-3,4-dihydro-2,2-dimethyl-3-pentafluoropropionyloxy-2H1-benzopyran, m.p. 126°-129° C. (recrystallized from hexaneethyl acetate (5:1)).

EXAMPLE 42

Trans-4-(N-benzyloxy-N-pentafluoropropionyl)amino-6-cyano-3,4-dihydro-2,2-dimethyl-2H-1-benzopyran-3-ol.

EXAMPLE 43

(1) Trans-6-cyano-3,4-dihydro-2,2-dimethyl-4-(N-hydroxy-N-pentafluoropropionyl)amino-2H-1-benzopyran-3-ol, m.p. 157°-159° C.

(2) Trans-6-cyano-3,4-dihydro-2,2-dimethyl-4-(N-hydroxy-N-pentafluoropropionyl)amino-3-pentafluoropropionyloxy-2H-1benzopyran.

EXAMPLE 44

Trans-4-(2-acetylhydrazino)-6-cyano-3,4-dihydro-2,2-dimethyl-2H-1-benzopyran-3-ol, 320 mg, was dissolved in 6 ml of chloroform and to this was added 0.5 ml of pyridine. While stirring under water cooling (20° C.), 0.23 ml of acetyl chloride was added and the mixture was stirred at room temperature for 3 hours. The solvent was distilled off under a reduced pressure, and to the residue was added ice water to scrape and crush it. After filtration and drying, it was recrystallized from ethyl acetate-hexane (1:1) to give 260 mg of trans-4-(1,2-diacetylhydrazino)-6-cyano-3,4-dihydro2,2-dimethyl-2H-1-benzopyran-3-ol as white crystals, m.p. 230°-233° C.

The compounds of Examples 45-49 were obtained in the same procedure as above, as illustrated hereinbelow.

EXAMPLE 45

Trans-4-(2-acetyl-1-propionylhydrazino)-6-cyano-3,4-dihydro-2,2-dimethyl-2H-1-benzopyran-3-ol, m.p. 144°-146° C. (decomposed) (recrystallized from hexane-ethanol). Monohydrate of the compound, m.p. 126°-128° C. (decomposed) (neutralized from its alkaline solution and deposited from water).

EXAMPLE 46

Trans-4-(2-acetyl-1-benzoylhydrazino)-6-cyano-3,4-dihydro-2,2-dimethyl-2H-1-benzopyran-3-ol, m.p. 220°-222° C. (decomposed) (recrystallized from hexane-ethanol).

EXAMPLE 47

Trans-4-(2-acetyl-1-nicotinoylhydrazino)-6-cyano-3,4-dihydro-2,2-dimethyl-2H-1-benzopyran-3-ol, m.p. 254°-255° C. (decomposition) (recrystallized from ethyl acetate-ethanol).

EXAMPLE 48

Trans-4-(2-acetyl-1-ethoxycarbonylhydrazino)-6-cyano3,4-dihydro-2,2-dimethyl-2H-1-benzopyran-3-ol, amorphous powders (purified by silica gel column chromatography and eluted.with chloroform-ethyl acetate (2:1)).

NMR ($d_6$—DMSO) δ: 1.20 (6H, m), 1.46 (3H, s), 1.90 (3H, s),
ca. 3.55 (1H, m), 4.15 (2H, q), 5.04 (1H, m), 5.44 (1H, d), 6.90 (1H, d), ca. 7.60 (1H, d), 7.63 (1H, s), 10.08 (1H, s).

EXAMPLE 49

Trans-4-(2-acetyl-1-ethylmalonylhydrazino)-6-cyano-3,4-dihydro-2,2-dimethyl-2H-1-benzopyran-3-ol, m.p. 171°-173° C. (recrystallized from hexane-ethanol).

EXAMPLE 50

Trans-4-(2-acetylhydrazino)-6-cyano-3,4-dihydro-2,2-dimethyl-2H-1-benzopyran-3-ol, 330 mg, was dissolved in 4 ml of chloroform, 0.3 ml of methyl isocyanate was added to this, and the mixture was heated on a water bath at 40° C. for 130 minutes. The solvent was distilled off under a reduced pressure and the residue obtained was recrystallized from ethyl acetate-ethanol to give 350 mg of trans-4-(2-acetyl-1-methylcarbamoylhydrazino)-6-cyano-3,4-dihydro-2,2-dimethyl-2H-1-benzopyran-3-ol·monohydrate as white crystals, m.p. 225°-226° C. (decomposed).

EXAMPLE 51

(1) Trans-4-(2-tert-butoxycarbonylhydrazino)-6-cyano3,4-dihydro-2,2-dimethyl-2H-1-benzopyran-3-ol, 1320 mg, was dissolved in 5 ml of chloroform, 1.3 ml of pyridine was added, and 0.75 ml of acetyl chloride was added with stirring under ice cooling. Stirring was continued at room temperature for 60 minutes and thereafter, the solvent was distilled off under reduced pressure. The residue was dissolved in 7 ml of methanol, 7 ml of a 10% aqueous solution of sodium hydroxide was added, and the solution was stirred at room temperature for 35 minutes. The solution was concentrated to result in the residue, to which ice water was added, whereby 1450 mg of nearly pure trans-4-(1-acetyl-2-tert-butoxycarbonylhydrazino)-6-cyano-3,4-dihydro-2,2-dimethyl-2H-1-benzopyran-3-ol was obtained as white crystals. When a portion of this product was recrystallized from hexane-ethyl acetate, it exhibited a melting point of 197°-198° C. (decomposed).

(2) The compound above, 1660 mg, was dissolved in 5 ml of trifluoroacetic acid to shake the solution at room temperature for 10 minutes, and the excess trifluoroacetic acid was distilled off under reduced pressure at room temperature. When ether-hexane (1:2) was added to the residue, trans-4(1-acetylhydrazino)-6-cyano-3,4-dihydro-2,2-dimethyl-2H-1-benzopyran-3-ol in a gum state was separated out. This was dried and dissolved in 5 ml of chloroform, and 2.5 ml of pyridine was added thereto. Further, 1.2 ml of propionyl chloride was added with stirring under cooling with water (20° C.) and stirring was continued at room temperature for 50 minutes. After the solvent was distilled off under reduced pressure, the residue was dissolved in 10 ml of methanol. To this was added 10 ml of a 10% aqueous solution of sodium hydroxide under water cooling, and stirring was continued at room temperature for 30 minutes. After the solvent had been distilled off completely, ice water was added, and extraction with ethyl acetate was effected. The organic layer so obtained was washed with an aqueous sodium chloride solution and filtered. The residue after concentration was recrystallized from hexane-ethyl acetate (1:1) to give 730 mg of trans-4(1-acetyl-2-propionylhydrazino)-6-cyano-3,4-dihydro-2,2-di-methyl-2H-1-benzopyran-3-ol, m.p. 201°–203° C.

EXAMPLE 52

Trans-4-(2-benzoylhydrazino)-6-cyano-3,4-dihydro-2,2-dimethyl-2H-1-benzopyran-3-ol (320 mg) was dissolved in 1 ml of chloroform, 0.5 ml of pyridine was added, and 0.28 ml of acetyl chloride was added with stirring under ice cooling. After stirring at room temperature for 80 minutes, the solvent was distilled off under reduced pressure and the residue was dissolved in 5 ml of methanol. The solution was treated with 5 ml of 1N-sodium hydroxide at room temperature for 30 minutes. After the methanol had been distilled off, the residue was shaken together with ethyl acetate-water and the organic layer was washed with an aqueous solution of sodium chloride and subsequently concentrated. This was recrystallized from hexane-ethanol (1:1) to give 170 mg of trans-4(1-acetyl-2-benzoylhydrazino)-6-cyano-3,4-dihydro-2,2-dimethyl-2H-1-benzopyran-3-ol monohydrate as white crystals, m.p. 212°–213° C.

EXAMPLE 53

A similar procedure to Example 52 was effected by using trans-4-(2-carbamoylhydrazino)-6-cyano-3,4-dihydro-2,2-di-methyl-2H-1-benzopyran-3-ol and acetyl chloride, and trans-4(1-acetyl-2-carbamoylhydrazino)-6-cyano-3,4-dihydro-2,2-di-methyl-2H-1-benzopyran-3-ol was thus obtained as white amorphous powders (purified by silica gel column chromatography and eluted with a 8:1 chloroform-methanol).

NMR (d$_6$—DMSO) δ: 1.23 (3H, s), 1.47 (3H, s), 2.12 (3H, s),
ca. 5.50 (1H, m), 5.76 (1H, s), 6.44 (2H, s), 6.92 (1H, d), 7.55–7.65 (2H, d+s), 8.65 (1H, s).

EXAMPLE 54

Trans-4-(1-acetyl-2-tert-butoxycarbonylhydrazino)-6-cyano-3,4-dihydro-2,2-dimethyl-2H-1-benzopyran-3-ol (560 mg) in Example 51(1) and 2 ml of trifluoro-acetic acid were treated in the same manner as Example 51(2), and the resulting compound eliminated of the protecting group was dissolved in 2 ml of chloroform. Then, triethylamine (0.22 ml) was added, 0.52 ml of methyl isocyanate was further added, and the mixture was sealed and allowed to stand at room temperature for 3 days. After the completion of the reaction, the solution was vacuum concentrated. To the residue, hexaneethanol (1:1) was added to scrape and crush it. Upon filtration, there was obtained an undissolved product, which was washed with water and dried. Trans-4-(1-acetyl-2-methyl-carbamoylhydrazino)-6-cyano-3,4-dihydro-2,2-dimethyl-3-N-methylcarbamoyloxy-2H-1-benzopyran (120 mg) was thus obtained as white crystals, m.p. 184°–185° C. (decomposed).

EXAMPLE 55

(1) Trans-4-(2-tert-butoxycarbonylhydrazino)-6-cyano3,4-dihydro-2,2-dimethyl-2H-1-benzopyran-3-ol (2150 mg) was dissolved in 6 ml of chloroform, 2.4 ml of pyridine was added, and while stirring under ice cooling, 1.5 ml of ethylmalonyl chloride was added. After cooling at 0° C. for 5 minutes, the mixture was stirred at room temperature for 60 minutes. The solvent was distilled off under reduced pressure and to the residue was added water. After extracted with ethyl acetate, the organic layer was washed with a dilute aqueous solution of potassium carbonate and an aqueous solution of sodium chloride, and concentrated. The resulting oily product, when separated by silica gel column chromatography (eluted with hexane-ethyl acetate (3:2)), gave 920 mg of trans-4-(2-tert-butoxycarbonyl-1-ethylmalonylhydrazino)6-cyano-3,4-dihydro-2,2-dimethyl-2H-1-benzopyran-3-ol as white crystals, m.p. 168°–169° C. (decomposed).

(2) The foregoing compound (530 mg) and 2 ml of trifluoroacetic acid were treated in a similar procedure to Example 51(2). The compound, eliminated of the protecting group, was dissolved in 9 ml of xylene, and 0.17 ml of triethylamine was added, and then, reflux heating was conducted for 70 minutes. After cooling, an undissolved product was obtained by filtration. Then it was washed with 10 ml of methanol and recrystallized from dimethylformamide-water to give 140 mg of trans-6-cyano-3,4-dihydro-2,2-dimethyl-4-(3,5-dioxopyrazolidin-1-yl)-2H-1-benzopyran-3-ol as white crystals, m.p. 280°–280.5° C. (decomposed).

EXAMPLE 56

A similar procedure to Example 55(1) was performed by using trans-4-(2-tert-butoxycarbonylhydrazino)-6-cyano-3,4-dihydro-2,2-dimethyl-2H-1-benzopyran-3-ol and ethylsuccinic chloride, thus producing trans-4-(2-tert-butoxycarbonyl-1ethylsuccinylhydrazino) 6-cyano-3,4-dihydro-2,2-dimethyl-2H1-benzopyran-3-ol, m.p. 184°–185° C. (decomposed) (recrystallized from hexane-ethanol).

Then, the compound above was eliminated of the protecting moiety in the same manner as Example 55(2) and further cyclized, whereby trans-6-cyano-3,4-dihydro-2,2-dimethyl-4( 3,6-dioxohexahydropyridazin-1-yl)-2H-1-benzopyran-3-ol was obtained, m.p. 252°–254° C. (decomposed) (washed with ethyl acetate under boiling).

EXAMPLE 57

(1) A similar procedure to Example 55(1) was performed by using 550 mg of trans-6-cyano-3,4-dihydro-2,2-dimethyl-4(2-methoxycarbonylhydrazino)-2H-1-benzopyran-3-ol dissolved in 1.5 ml of chloroform, 0.4 ml of pyridine, and 0.22 ml of acetyl chloride. An oily crude product was thus obtained and, when recrystallized from hexane-ethanol (1:1) twice, yielded 70 mg of trans-4-(1-acetyl-2-methoxy-carbonylhydra-zino)-6-cyano-3,4-dihydro-2,2-dimethyl-3-acetoxy-2H-1-benzopyran, m.p. 213°–214° C.

(2) The filtrate after recrystallization was concentrated and column chromatographed on silica gel by eluting with chloroform-methanol (15:1). Thus, trans-4-(1-acetyl2-methoxycarbonylhydrazino)-6-cyano-3,4-dihydro-2,2-dimethyl2H-1-benzopyran-3-ol, 65 mg, was obtained as white crystals, m.p. 192°–194° C. (decomposed).

In the same procedure as any of the examples above, the compounds of Examples 58-65 can be obtained.

EXAMPLE 58

The compound of Reference Example 2 (530 mg) was dissolved in a mixture of 2 ml of chloroform and 1.1 ml of pyridine, and to this was added, with stirring under water cooling, 0.82 ml of acetyl chloride in several divided portions. Stirring was continued at 40° C. for 40 minutes and subsequently, the solvent was distilled off under reduced pressure. The residue, after addition of water thereto, was extracted with ethyl acetate, washed with water, and treated with activated charcoal, followed by concentration. This was column chromatographed on silica gel and eluted with chloroform-ethyl acetate (1:3). The concentrated product was scraped and crushed with hexane-ethyl acetate to give 300 mg of trans-3-acetoxy-4-(1,2-diacetylhydrazino)-6-cyano-3,4-dihydro-2,2-dimethyl-2H-1-benzopyran in yellow amorphous powders.

NMR (d$_6$—DMSO) δ: 1.20 (3H, s), 1.32 (3H, s), 1.87 (3H, s),
1.91 (3H, s), 2.07 (3H, s), 4.85-5.60 (2H, broad m),
6.92 (1H, d), 7.59 (1H, d), 7.88 (1H, m), 10.12 (1H, s).

EXAMPLE 59

Trans-4-(1-acetyl-2-formylhydrazino)-6-cyano-3,4-dihydro-2,2-dimethyl-2H-1-benzopyran-3-ol.monohydrate, m.p. 147°-150° C. (decomposed), (recrystallized from hexane-ethanol (1:1)).

EXAMPLE 60

Trans-4-(1,2-diacetylhydrazino)-3,4-dihydro-2,2-dimethyl6-nitro-2H-1-benzopyran-3-ol, m.p. 212°-214° C. (recrystallized from hexane-ethanol (1:1)).

EXAMPLE 61

Trans-4-(1,2-diacetylhydrazino)-6-chloro-3,4-dihydro2,2-dimethyl-2H-1-benzopyran-3-ol, m.p. 250.5°-251° C. (decomposed) (recrystallized from hexane-ethanol (6:1)).

EXAMPLE 62

Trans-4-(1,2-diacetylhydrazino)-3,4-dihydro-2,2-dimethyl-6-methylsulfonyl-2H-1-benzopyran-3-ol.

EXAMPLE 63

Trans-4-(1,2-diacetylhydrazino)-3,4-dihydro-2,2-dimethyl-6-phenysulfonyl-2H-1-benzopyran-3-ol, m.p. 150°-155° C. (recrystallized from hexane-ethanol (2:1)).

EXAMPLE 64

Trans-4-(1,2-diacetylhydrazino)-6-cyano-3,4-dihydro-3-hydroxy-2H-1-benzopyran-2-spiro-1'-cyclohexane, m.p. 246.5°-248° C. (decomposed) (recrystallized from hexane-ethanol (3:1)).

EXAMPLE 65

Trans-4-(1-acetyl-2-hydroxyacetylhydrazino)-6-cyano-3,4-dihydro-2,2-dimethyl-2H-benzopyran-3-ol.

EXAMPLE 66

(1) A similar procedure to Reference Example 2 was performed by using (−)-6-cyano-3,4-epoxy-3,4-dihydro-2,2-dimethyl-2H-1-benzopyran and acetohydrazide, whereby (+)-(3S,4R)-trans-4-(2-acetylhydrazino)-6-cyano-3,4-dihydro-2,2-dimethyl-2H-1-benzopyran-3-ol was obtained, m.p. 164°-165.5° C., $[\alpha]_D^{23}$= +338.1° (C=1, CHCl$_3$).

(2) (+)-(3S,4R)-Trans-4-(2-acetylhydrazino)-6-cyano-3,4-dihydro-2,2-dimethyl-2H-1-benzopyran-3ol obtained in (1) above and acetyl chloride were made to react in a similar procedure to Example 44 and by the recrystallization from hexane-ethanol (3:1), (−)-(3S,4R)-trans-4-(1,2-diacetylhydrazino)-6-cyano-3,4-dihydro-2,2-dimethyl-2H-1-benzopyran-3-ol was obtained, m.p. 205°-207° C., $[\alpha]_D^{23}$= −73.9° (C=1, CHCl$_3$).

EXAMPLE 67

(1) (+)-6-Cyano-3,4-epoxy-3,4-dihydro-2,2-dimethyl-2H-1-benzopyran and acetohydrazide were made to react in the same procedure as Reference Example 2 whereby (−) -(3R,4S)-trans-4-(2-acetylhydrazino)-6-cyano-3,4-dihydro-2,2-dimethyl-2H-1-benzopyran-3-ol was obtained, m.p. 164°-167° C., $[\alpha]_D^{23}$= -335.2° (C=1, CHCl$_3$).

(2) (−)-(3R,4S)-Trans-4-(2-acetylhydrazino)-6-cyano-3,4-dihydro-2,2-dimethyl-2H-b 1-benzopyran-3-ol obtained in (1) above and acetyl chloride were subjected to reaction in the same procedure as Example 44 and the recrystallization from hexane-ethanol (3:1) afforded (+)-3R,4S)-trans-4-(1,2-diacetylhydrazino)-6-cyano-3,4-dihydro-2,2-dimethyl-2H-1-benzopyran-3-ol, m.p. 205.5°-207° C., $[\alpha]_D^{23}$= +75.4° (C=1, CHCl$_3$).

EXAMPLE 68

(1) (−)-3,4-Epoxy-3,4-dihydro-2,2-dimethyl-6-nitro-2H-1-benzopyran and acetohydrazide were made to react in the same procedure as Reference Example 2 whereby (+)-(3S,4R)-trans-4-(2-acetylhydrazino)-3,4-dihydro-2,2-dimethyl-6-nitro-2H-1-benzopyran-3-ol was obtained, m.p. 175.5°-176° C., $[\alpha]_D^{24}$= +393.0° (C=1, CHCl$_3$).

(−)-(3R,4S)-Trans-4-(2acetylhydrazino)-3,4-dihydro-2,2-dimethyl-6-nitro-2H-1-benzopyran-3-ol, m.p. 175°14 176° C., $[\alpha]_D^{24}$= −391.2° (C=1, CHCl$_3$).

(2) Then, this compound and acetyl chloride were allowed to react in the same procedure as Example 44 thereby to produce (−)-(3S,4R)-trans-4-(1,2-diacetylhydrazino)-3,4-dihydro-2,2-dimethyl-6-nitro-2H-1-benzopyran-3ol.1/3 ethyl acetate solvate, m.p. 114°-120° C. (gradually decomposed), $[\alpha]_D^{24}$= 11.1° (C=1, CHCl$_3$) (recrystallized from n-hexaneethyl acetate).

(=)-(3R,4S)-Trans-4-(1,2-diacetylhydrazino)-3,4-dihydro-2,2-dimethyl-6-nitro-2H-1-benzopyran-3-ol.1/3 ethyl acetate solvate, m.p. 110°-12020 C., (gradually decomposed), $[\alpha]_D^{24}$= +10.4° (C=1, CHCl$_3$) (recrystallized from n-hexane-ethyl acetate).

We claim:

1. A benzopyran compound of the formula (I)

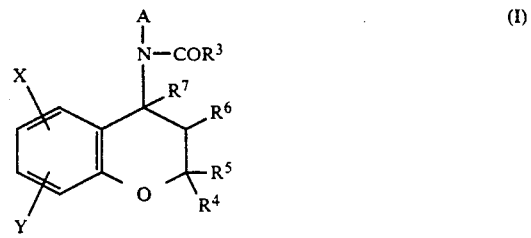

wherein A represents —OR$^1$ (wherein R$^1$ represents hydrogen, lower alkyl, formyl, alkanoyl, benzoyl, naphthoyl, phenylalkyl or naphthylalkyl having, as the alkyl moieties, straight- or branched-chain alkyls having 1 to 4 carbon atoms, or a phenylalkyl or a naphthylalkyl each substituted on the aromatic ring by at least one of halogen, lower alkyl, lower alkoxy, hydroxy, trifluoromethyl, cyano, nitro and amino); $R^3$ represents furyl, pyridyl, thienyl, or furyl, pyridyl or thienyl each substituted by at least one of halogen, lower alkyl, lower alkoxy, hydroxy, trifluoromethyl, cyano, nitro, or amino; $R^4$ and $R^5$ are the same or different, and respectively represent hydrogen or lower alkyl, or together form an alkylene having 2 to 5 carbon atoms; $R^6$ represents hydroxy, formyloxy, alkanoyloxy, haloalkanoyloxy, lower alkoxycarbonyloxy, benzoyloxy, naphthoyloxy, furoyloxy, pyridylcarbonyloxy, thienoyloxy, carbamouloxy, mono- or di- lower alkylcarbomoyloxy and $R^7$ represent hydrogen, or $R^6$ and $R^7$ together form a bond and, X and Y are the same or different, and respectively represent hydrogen, halogen, nitro, cyano, lower alkyl, lower alkoxy, halo-lower alkyl, carboxyl, formyl, alkanoyl, benzoyl, naphthoyl, haloalkanoyl, carbamoyl, lower alkylsulfinyl, phenylsulfinyl, naphthylsulfinyl, or a phenylsulfinyl or a naphthylsulfinyl each substituted on the aromatic ring by at least one of halogen, lower alkyl, lower alkoxy, hydroxy, trifluoromethyl, cyano, nitro or amino, lower alkylsulfonyl, phenylsulfonyl, naphthylsulfonyl, or a phenylsulfonyl or a naphthylsulfonyl each substituted on the aromatic ring by at least one of halogen, lower alkyl, lower alkoxy, hydroxy, trifluoromethyl, cyano, nitro or amino, sulfonamido or mono- or di-alkylsulfonamido having, as the alkyl moieties, straight- or branched-chain alkyls having 1 to 6 carbon atoms, or a pharmaceutically acceptable salt thereof.

2. The benzopyran compound as claimed in claim 1 which is trans-6-cyano-3,4-dihydro-2,2-dimethyl-4-[N-(2-furoyl)-N-hydroxy]amino-2H-1-benzopyran-3-ol or a pharmaceutically acceptable salt thereof.

3. The benzopyran compound as claimed in claim 1 which is trans-6-cyano-3,4-dihydro-2,2-dimethyl-4-(N-hydroxy-N-nicotinoyl)amino-2H-1-benzopyran-3-ol or a pharmaceutically acceptable salt thereof.

4. The benzopyran compound as claimed in claim 1 which is (−)-(3S,4R)-trans-6-cyano-3,4-dihydro-2,2-dimethyl- 4-(N-hydroxy-N-nicotinoyl)amino-2H-1-benzopyran-3-ol or a pharmaceutically acceptable salt thereof.

5. A pharmaceutical composition which contains, as the effective ingredient, the compound as claimed in claim 2.

6. A pharmaceutical composition which contains, as the effective ingredient, the compound as claimed in claim 3.

7. A pharmaceutical composition which contains, as the effective ingredient, the compound as claimed in claim 4.

* * * * *